United States Patent
Tsujimoto

(10) Patent No.: US 11,328,522 B2
(45) Date of Patent: May 10, 2022

(54) LEARNING DEVICE, METHOD, AND PROGRAM FOR DISCRIMINATOR, AND DISCRIMINATOR

(71) Applicant: FUJIFILM Corporation, Tokyo (JP)

(72) Inventor: Takayuki Tsujimoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 163 days.

(21) Appl. No.: 16/774,123

(22) Filed: Jan. 28, 2020

(65) Prior Publication Data
US 2020/0160027 A1 May 21, 2020

Related U.S. Application Data

(63) Continuation of application No. PCT/JP2018/021742, filed on Jun. 6, 2018.

(30) Foreign Application Priority Data

Aug. 25, 2017 (JP) .............................. JP2017-162052

(51) Int. Cl.
*G06V 20/00* (2022.01)
*G06V 20/69* (2022.01)
(Continued)

(52) U.S. Cl.
CPC .............. *G06V 20/695* (2022.01); *B01L 3/50* (2013.01); *G01N 23/041* (2018.02);
(Continued)

(58) Field of Classification Search
CPC .. G06K 9/0014; G06K 9/6256; G06K 9/6262; G01N 23/041; G01N 33/4833; B01L 3/50; B01L 2300/0663
See application file for complete search history.

(56) References Cited

U.S. PATENT DOCUMENTS

2012/0092478 A1 4/2012 Honda et al.
2012/0114219 A1 5/2012 Nakagawa et al.
(Continued)

FOREIGN PATENT DOCUMENTS

EP 3375859 A1 9/2018
JP 2002156272 A 5/2002
(Continued)

OTHER PUBLICATIONS

Hao Tong et al., "Cross domain mitotic cell recognition", Neurocomputing, Elsevier, Feb. 12, 2016, pp. 6-12, vol. 195, ISSN: 0925-2312, Amsterdam, NL.
(Continued)

*Primary Examiner* — Nancy Bitar
*Assistant Examiner* — Xiao Liu
(74) *Attorney, Agent, or Firm* — Studebaker & Brackett PC

(57) ABSTRACT

In a learning device, method, and program for a discriminator, and a discriminator, it is possible to enable accurate learning of a discriminator that discriminates a state of an object to be observed, such as a cell. An image acquisition unit acquires a first image including an influence of a meniscus and a second image with the influence of the meniscus eliminated for the same object to be observed. Next, a training data generation unit generates training data for learning a discriminator based on the second image. Then, a learning unit learns the discriminator based on the first image and the training data.

11 Claims, 6 Drawing Sheets

(51) Int. Cl.
   *G01N 23/041* (2018.01)
   *B01L 3/00* (2006.01)
   *G01N 33/483* (2006.01)
   *G06K 9/62* (2022.01)

(52) U.S. Cl.
   CPC ....... *G01N 33/4833* (2013.01); *G06K 9/6256* (2013.01); *G06K 9/6262* (2013.01); *B01L 2300/0663* (2013.01)

(56) References Cited

U.S. PATENT DOCUMENTS

| | | | |
|---|---|---|---|
| 2013/0163844 | A1 | 6/2013 | Ozaki et al. |
| 2014/0270431 | A1 | 9/2014 | Xu et al. |
| 2016/0035093 | A1* | 2/2016 | Kateb .................. G02B 23/24 382/131 |
| 2017/0322405 | A1 | 11/2017 | Matsubara |
| 2018/0113294 | A1 | 4/2018 | Shiraishi |
| 2018/0113295 | A1 | 4/2018 | Matsubara |
| 2018/0129028 | A1 | 5/2018 | Murooka |
| 2018/0267286 | A1* | 9/2018 | Bonzon ................ C12M 23/12 |
| 2018/0322660 | A1* | 11/2018 | Smith .................. G06K 9/6267 |
| 2018/0330511 | A1* | 11/2018 | Ha ...................... G06K 9/6203 |
| 2019/0033569 | A1 | 1/2019 | Shiraishi |
| 2020/0013146 | A1* | 1/2020 | Yasuda ............... G06T 3/4053 |

FOREIGN PATENT DOCUMENTS

| | | |
|---|---|---|
| JP | 2013128438 A | 7/2013 |
| JP | 2013174823 A | 9/2013 |
| JP | 2016049055 A | 4/2016 |
| JP | 2016071117 A | 5/2016 |
| JP | 2017085966 A | 5/2017 |
| JP | 2018077337 A | 5/2018 |
| WO | 2010098105 A1 | 9/2010 |
| WO | 2011010449 A1 | 1/2011 |
| WO | 2016/084551 A1 | 6/2016 |
| WO | 2016/120757 A1 | 8/2016 |
| WO | 2017002451 A1 | 1/2017 |
| WO | 2017002458 A1 | 1/2017 |
| WO | 2017145839 A1 | 8/2017 |
| WO | 2017163378 A1 | 9/2017 |

OTHER PUBLICATIONS

The extended European search report issued by the European Patent Office dated Jul. 14, 2020, which corresponds to European Patent Application No. 18848312.7-1020 and is related to U.S. Appl. No. 16/774,123.

An Office Action mailed by the Korean Intellectual Property Office dated Dec. 3, 2020, which corresponds to Korean Patent Application No. 10-2020-7003281 and is related to U.S. Appl. No. 16/774,123 with English language translation.

International Search Report issued in PCT/JP2018/021742; dated Sep. 4, 2018.

International Preliminary Report on Patentability and Written Opinion issued in PCT/JP2018/021742; dated Feb. 25, 2020.

Communication pursuant to Article 94(3) EPC issued by the European Patent Office dated Sep. 7, 2021, which corresponds to European Patent Application No. 18848312.7-1020 and is related to U.S. Appl. No. 16/774,123.

* cited by examiner

LEARNING DEVICE, METHOD, AND PROGRAM FOR DISCRIMINATOR, AND DISCRIMINATOR

CROSS-REFERENCE TO RELATED APPLICATIONS

This application is a Continuation of PCT International Application No. PCT/JP2018/021742 filed on Jun. 6, 2018, which claims priority under 35 U.S.C § 119(a) to Japanese Patent Application No. 2017-162052 filed on Aug. 25, 2017. Each of the above application(s) is hereby expressly incorporated by reference, in its entirety, into the present application.

BACKGROUND OF THE INVENTION

1. Field of the Invention

The present invention relates to a learning device, method, and program for a discriminator, which discriminates a state of an object to be observed using an image of a container where a liquid having a concave liquid surface and the object to be observed are contained, and a discriminator that discriminates the state of the object to be observed.

2. Description of the Related Art

A multipotential stem cell, such as an embryonic stem (ES) cell or an induced pluripotent stem (iPS) cell, has the ability to differentiate into cells of various tissues, and is attracting attention as being applicable in regenerative medicine, development of medicines, explanation of diseases, or the like.

In the related art, a method that specifies a differentiation state or the like of a cell by imaging a multipotential stem cell, such as an ES cell or an iPS cell, a differentiated and induced cell, or the like using a microscope, such as a phase contrast microscope, and capturing a feature of an image acquired through imaging has been suggested.

For example, in JP2013-128438A, a method that discriminates a state of a cell included in an image acquired through imaging using a discriminator, which has learned the state of the cell in advance, has been suggested. Such a discriminator outputs a discrimination result of a state of a pixel position to be discriminated in a case where a feature quantity of the pixel position to be discriminated in the image acquired through imaging is input. In JP2013-128438A, an image in which a state of a cell acquired in advance is known is learned as training data, whereby the discriminator is generated.

On the other hand, as described above, in imaging the cell with the microscope, a technique in which so-called tiling imaging is performed in order to acquire a high-magnification wide view image has been suggested. Specifically, for example, a method that scans each observation region inside a well by moving a stage, on which the well plate and the like is provided, with respect to an imaging optical system, captures an image of each observation region, and connects the images of the observation regions has been suggested.

SUMMARY OF THE INVENTION

Here, in cultivating a cell using the above-described well plate or the like, while the cell and a liquid, such as a culture solution are contained in the well, it is known that a meniscus is formed on the surface of the liquid.

In particular, in a case where an image of a cell is captured using a phase contrast microscope device, an influence of a meniscus on a captured image is large. Due to the influence of the meniscus, a meniscus region where a meniscus is formed becomes an image with low contrast compared to a captured image of a non-meniscus region where a meniscus is not formed. Accordingly, in the captured image including the meniscus region, it is not possible to extract an image of an individual cell with high accuracy.

Here, the above-described discriminator that discriminates the state of the cell creates training data from the captured image including the meniscus region. However, it is not possible to extract the individual cell from the captured image including the meniscus region with high accuracy. Accordingly, even though training data created from the captured image including the meniscus region is used, the discriminator cannot be learned with excellent accuracy, and as a result, the discrimination accuracy of the discriminator is also degraded.

The invention has been accomplished in consideration of the above-described situation, and an object of the invention is to enable a discriminator, which discriminates a state of an object to be observed, such as a cell, to be learned with excellent accuracy.

According to an aspect of the invention, there is provided a learning device for a discriminator, which discriminates a state of an object to be observed based on a captured image including an influence of a meniscus acquired by imaging a container, in which a liquid with a meniscus formed on a surface and an object to be observed are contained. The learning device comprises an image acquisition unit that acquires a first image including the influence of the meniscus and a second image with the influence of the meniscus eliminated for the same object to be observed, a training data generation unit that generates training data for learning the discriminator based on the second image, and a learning unit that learns the discriminator based on the first image and the training data.

In a case of imaging the container in which the liquid with the meniscus formed on the surface and the object to be observed are contained, light incident on the container is refracted in a meniscus region where the meniscus is formed in the container and moves forward in a non-meniscus region where no meniscus is formed. With this, in an image acquired by imaging, the meniscus region becomes higher in brightness than the non-meniscus region, and contrast is degraded. In particular, in a case of imaging the container with the phase contrast microscope, since light passing through the non-meniscus region passes through a phase plate, light undergoes weakening of amplitude and phase shift, and is combined with diffracted light by the object to be observed to become an image with high contrast. On the other hand, since there is a possibility that light passing through the meniscus region does not pass through the phase plate, light does not undergo change in amplitude and phase, and becomes an image with low contrast and high brightness.

The "image including the influence of the meniscus" means an image in which a region with low contrast and high brightness obtained by light passing through the meniscus region in the image is included.

In the learning device according to the aspect of the invention, the second image may be acquired by imaging the object to be observed with the liquid eliminated.

In the learning device according to the aspect of the invention, the second image may be acquired by imaging the object to be observed in the container filled with the liquid and sealed with a transparent plate.

In the learning device according to the aspect of the invention, the second image may be acquired by imaging the object to be observed with an imaging device comprising an optical element configured to eliminate the influence of the meniscus.

In the learning device according to the aspect of the invention, the training data generation unit may generate an image obtained by applying a label according to the state of the object to be observed to the second image or the second image as the training data.

In the learning device according to the aspect of the invention, the discriminator may have a feature quantity of a pixel to be an object to be discriminated in the captured image as input, and may output a discrimination result of the state of the object to be observed for the pixel to be the object to be discriminated.

In the learning device according to the aspect of the invention, the captured image may be acquired by imaging the container with a phase contrast microscope.

The learning unit may collate a discrimination result output from the discriminator for a pixel to be discriminated in the first image with a pixel in the training data corresponding to the pixel to be discriminated to learn the discriminator.

According to another aspect of the invention, there is provided a discriminator learned by the learning device for a discriminator according to the aspect of the invention.

According to still another aspect of the invention, there is provided a learning method for a discriminator, which discriminates a state of an object to be observed based on a captured image including an influence of a meniscus acquired by imaging a container, in which a liquid with a meniscus formed on a surface and the object to be observed are contained. The learning method comprises acquiring a first image including the influence of the meniscus and a second image with the influence of the meniscus eliminated for the same object to be observed, generating training data for learning the discriminator based on the second image, and learning the discriminator based on the first image and the training data.

According to still another aspect of the invention, there is provided a learning program for a discriminator that causes a computer to execute a step of discriminating a state of an object to be observed based on a captured image including an influence of a meniscus acquired by imaging a container, in which a liquid with a meniscus formed on a surface and the object to be observed are contained, a step of acquiring a first image including the influence of the meniscus and a second image with the influence of the meniscus eliminated for the same object to be observed, a step of generating training data for learning the discriminator based on the second image, and a step of learning the discriminator based on the first image and the training data.

According to still another aspect of the invention, there is provided a learning device for a discriminator, which discriminates a state of an object to be observed based on a captured image including an influence of a meniscus acquired by imaging a container, in which a liquid with a meniscus formed on a surface and an object to be observed are contained. The learning device comprises a memory that stores commands to be executed by a computer, and a processor configured to execute the stored commands. The processor executes processing for acquiring a first image including the influence of the meniscus and a second image with the influence of the meniscus eliminated for the same object to be observed, generating training data for learning the discriminator based on the second image, and learning the discriminator based on the first image and the training data.

According to the aspects of the invention, the first image including the influence of the meniscus and the second image with the influence of the meniscus eliminated for the same object to be observed are acquired, and the training data for learning the discriminator that discriminates the state of the object to be observed based on the second image is generated. Then, the discriminator is learned based on the first image including the influence of the meniscus and the training data. With this, it is possible to accurately learn the discriminator that discriminates the state of the object to be observed, such as a cell.

DESCRIPTION OF THE PREFERRED EMBODIMENTS

Figure 1:
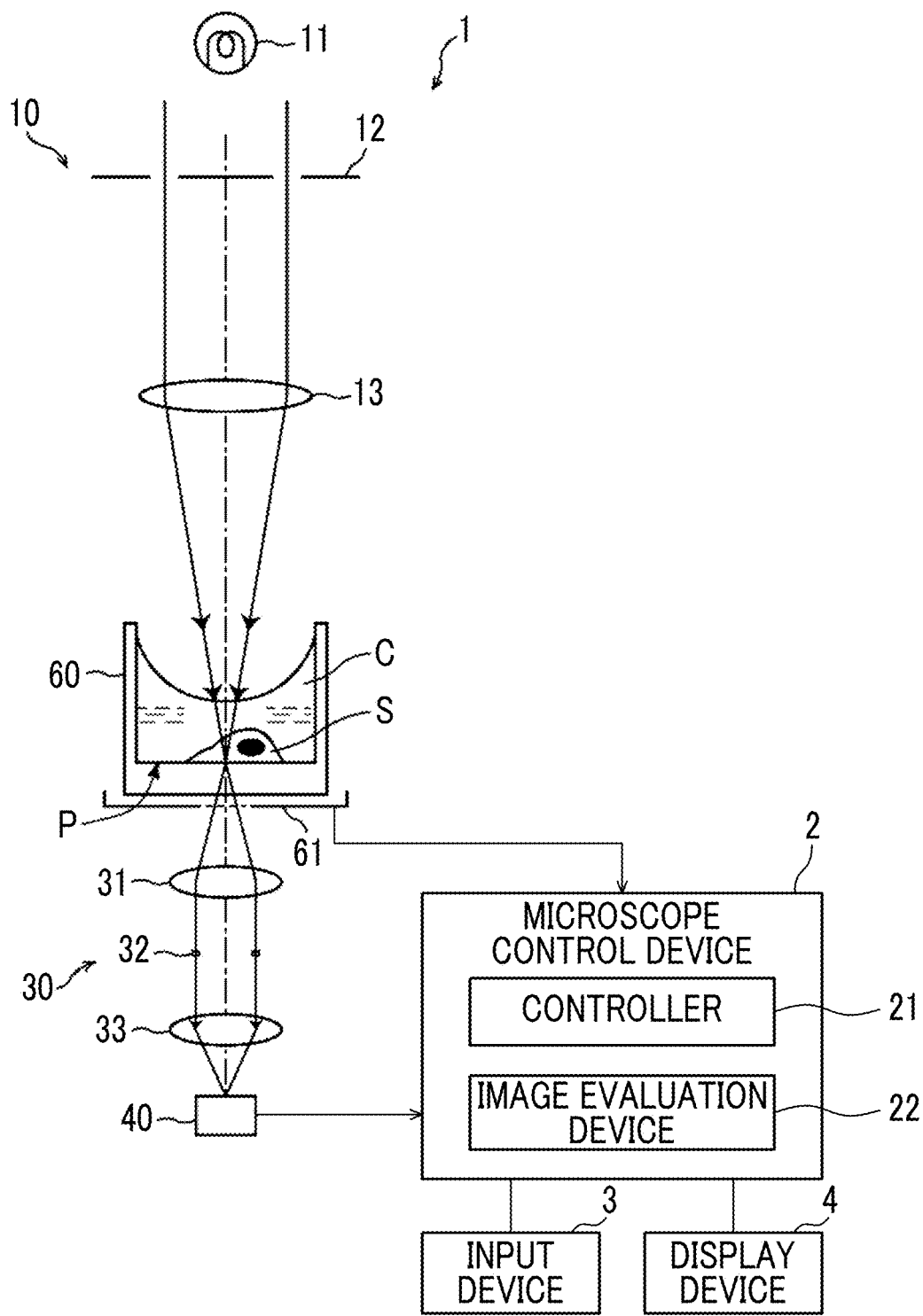
FIG. 1 is a diagram showing the schematic configuration of an embodiment of an image evaluation system to which a learning device for a discriminator of the invention is applied.

Hereinafter, an embodiment of the invention will be described. FIG. 1 is a diagram showing the schematic configuration of an image evaluation system to which a learning device for a discriminator according to an embodiment of the invention is applied. As shown in FIG. 1, the image evaluation system of the embodiment comprises a microscope device 1, a microscope control device 2, an input device 3, and a display device 4.

In the embodiment, the microscope device 1 is a phase contrast microscope, and captures, as a captured image, a phase contrast image of, for example, a cultivated cell as an object to be observed. Specifically, as shown in FIG. 1, the microscope device 1 comprises an illumination light irradiation unit 10, an imaging optical system 30, a stage 61, and an imaging unit 40. The microscope device 1 of the embodiment is an example of an imaging device of the present disclosure.

A cultivation container 60 in which an object S to be observed, such as a cell, and a culture solution C are contained is placed on the stage 61. A rectangular opening is formed at the center of the stage 61. The cultivation container 60 is installed on a member that forms the opening, and light passing through the object S to be observed in the cultivation container 60 and light diffracted by the object S to be observed pass through the opening.

As the cultivation container 60, for example, while a well plate having a plurality of wells (corresponding to a container of the invention) is used, the invention is not limited thereto, and a schale, a dish, or the like may be used. As the object S to be observed that is contained in the cultivation container 60, multipotential stem cells, such as an iPS cell and an ES cell, cells of nerve, skin, myocardium, and liver differentiated and induced from a stem cell, cells of skin, retina, myocardium, blood corpuscles, nerves, and organs, and the like may be used.

A bottom surface of the cultivation container 60 placed on the stage 61 is an installation surface P of the object S to be observed, and the object S to be observed is disposed on the installation surface P. The cultivation container 60 is filled with the culture solution C, and a meniscus having a concave shape is formed on a liquid surface of the culture solution C. In the embodiment, while a cell cultivated in the culture solution is used as the object S to be observed, the object S to be observed is not limited to the cell in the culture solution, and a cell fixed in a liquid, such as water, formalin, ethanol, or methanol, may be used as the object S to be observed. Even in this case, a meniscus is formed on the liquid surface of the liquid in the container.

The illumination light irradiation unit 10 irradiates the object S to be observed contained in the cultivation container 60 on the stage 61 with illumination light for so-called phase contrast measurement. In the embodiment, the illumination light irradiation unit 10 irradiates ring-shaped illumination light as illumination light for phase contrast measurement.

Specifically, the illumination light irradiation unit 10 of the embodiment comprises a white light source 11 that emits white light for phase contrast measurement, a slit plate 12 that has a ring-shaped slit, on which white light emitted from the white light source 11 is incident, and that emits ring-shaped illumination light, and a condenser lens 13 on which receives ring-shaped illumination light emitted from the slit plate 12 is incident, and that irradiates the object S to be observed with the received ring-shaped illumination light.

The slit plate 12 is provided with the ring-shaped slit that transmits white light in a light shielding plate configured to shield white light emitted from the white light source 11, and as white light passes through the slit, ring-shaped illumination light is formed. The condenser lens 13 converges ring-shaped illumination light emitted from the slit plate 12 toward the object S to be observed.

In the cultivation container 60 placed on the stage 61, a cultivated cell group (cell colony) is disposed as the object S to be observed. As the cultivated cells, multipotential stem cells, such as an iPS cell and an ES cell, cells of nerve, skin, myocardium, and liver differentiated and induced from a stem cell, cells of skin, retina, myocardium, blood corpuscles, nerves, and organs, and the like may be used. As the cultivation container 60, a well plate in which a schale and a plurality of wells are arranged, or the like can be used. In a case where the well plate is used, each well corresponds to a container of the invention. In the embodiment, the well plate in which a plurality of wells are arranged is used as the cultivation container 60.

The imaging optical system 30 forms an image of the object S to be observed in the cultivation container 60 on the imaging unit 40. The imaging optical system 30 comprises an objective lens 31, a phase plate 32, and an imaging lens 33.

In the phase plate 32, a phase ring is formed in a transparent plate that is transparent with respect to a wavelength of ring-shaped illumination light. The size of the slit of the slit plate 12 described above has a relationship conjugate with the phase ring.

In the phase ring, a phase membrane that shifts the phase of incident light by ¼ wavelength, and a dimmer filter that dims incident light are formed in a ring shape. Direct light incident on the phase plate 32 passes through the phase ring, and thus, the phase thereof is shifted by a ¼ wavelength and the brightness thereof is weakened. On the other hand, most of diffracted light diffracted by the object S to be observed passes through a portion of the transparent plate of the phase plate 32, and thus, the phase and brightness thereof are not changed.

The imaging lens 33 is a member on which direct light and diffracted light passing through the phase plate 32 are incident, and that and forms images of direct light and diffracted light on the imaging unit 40.

The imaging unit 40 comprises an imaging element that receives an image of the object S to be observed formed by the imaging lens 33, images the object S to be observed, and outputs a phase contrast image as an observation image. As the imaging element, a charge-coupled device (CCD) image sensor, a complementary metal-oxide semiconductor (CMOS) image sensor, or the like can be used.

Here, the stage 61 is driven by a stage drive unit (not shown) and moves in an X direction and a Y direction perpendicular to each other within a horizontal plane. With the movement of the stage 61, each observation region in each well of the well plate is scanned, and a captured image of each observation region is acquired by the imaging unit 40. The captured image of each observation region is output to the microscope control device 2.

Figure 2:
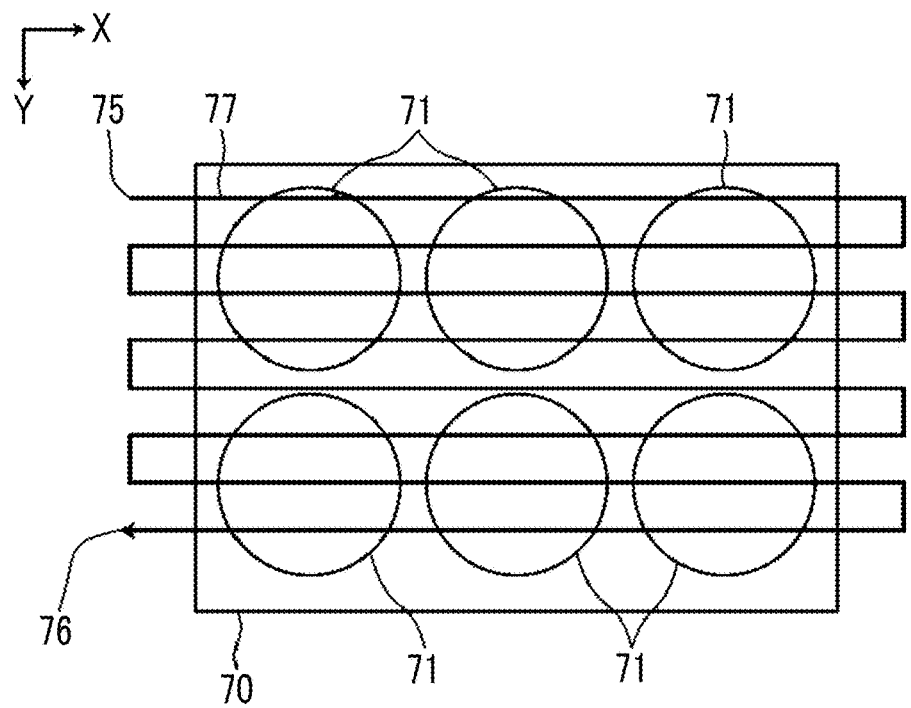
FIG. 2 is a diagram showing a scanning locus of each observation region in a well plate.

FIG. 2 is a diagram in which the scanning locus of each observation region is indicated by a solid line 77 in a case where a well plate 70 having six wells 71 is used. As shown in FIG. 2, each observation region in the well plate 70 is scanned from a scanning start point 75 to a scanning end point 76 along the solid line 77 with the movement of the stage 61 in the X direction and the Y direction.

In the embodiment, although the captured image of each observation region in the well is acquired with the movement of the stage 61, the invention is not limited thereto, and the imaging optical system 30 may be moved with respect to the stage 61 to acquire the captured image of each observation region. Alternatively, both of the stage 61 and the imaging optical system 30 may be moved.

The microscope control device 2 is constituted of a computer comprising a central processing unit (CPU), a semiconductor memory, a hard disk, and the like. Then, a program that includes a learning program for a discriminator of the invention and controls the system is installed in the hard disk. As the program is executed by the CPU, the CPU functions as the respective units of the microscope control device 2. The microscope control device 2 controls the entire image evaluation system. As shown in FIG. 1, the microscope control device 2 comprises a controller 21 and an image evaluation device 22.

The controller 21 controls the drive of the illumination light irradiation unit 10, the stage drive unit (not shown) that drives the stage 61, the imaging optical system 30, and the imaging unit 40 to acquire the captured image of the object S to be observed.

Figure 3:
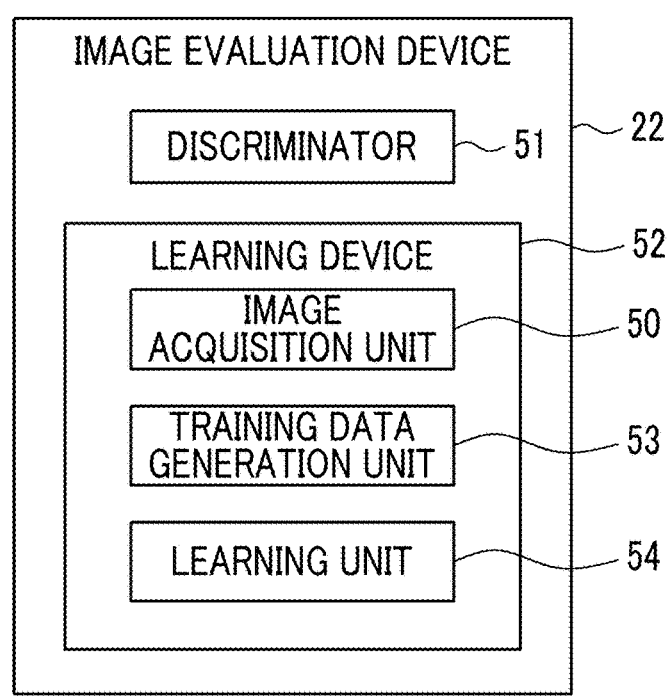
FIG. 3 is a schematic block diagram showing the configuration of an image evaluation device.

The image evaluation device 22 evaluates a state of the object S to be observed included in the captured image. FIG. 3 is a schematic block diagram showing the configuration of the image evaluation device 22. As shown in FIG. 3, the image evaluation device 22 comprises a discriminator 51 and a learning device 52 for the discriminator 51. The learning device 52 comprises an image acquisition unit 50, a training data generation unit 53, and a learning unit 54.

In the embodiment, the image evaluation device 22 acquires a captured image of each observation region and evaluates a state of an object S to be observed included in the captured image. In the embodiment, the object S to be observed is a cell. For this reason, evaluating the state of the object S to be observed refers to, for example, evaluating whether the cell include in the captured image is an undifferentiated cell or a differentiated cell, evaluating whether a differentiated cell is in a differentiated state or in the middle of differentiation, evaluating the ratio of an undifferentiated cell and a differentiated cell included in the captured image, evaluating the degree of growth of the cell or a cell colony, or evaluating a reduction rate of a cancer cell by a carcinostatic agent. It should be noted that the evaluation of the state of the cell is not limited thereto, and other evaluations may be applied. In the embodiment, it is assumed that, in a case where the cell is a differentiated cell, the image evaluation device 22 evaluates whether the cell is in the differentiated state or in the middle of differentiation.

The image acquisition unit 50 acquires the captured image of the object S to be observed captured by the imaging unit 40. In the embodiment, since the cultivation container 60 is the well plate in which a plurality of wells are arranged, the captured image of each observation region in each well is acquired.

The discriminator 51 outputs a discrimination result for the captured image. In the embodiment, the image evaluation device 22 evaluates whether the cell is in the differentiated state or in the middle of differentiation. For this reason, the discriminator 51 outputs a discrimination result regarding whether the cell included in the captured image is in the differentiated state or in the middle of differentiation. In order to perform such discrimination, the discriminator 51 has a feature quantity of a pixel to be discriminated to be an object to be discriminated in the captured image as input, and is machine-learned so as to output a discrimination result of a state of the pixel to be discriminated. In the embodiment, the discriminator 51 uses, as input, a pixel value in a region determined in advance centering on the pixel to be discriminated in the captured image as the feature quantity as input, and outputs three discrimination results of a cell in the differentiated state, a cell in the middle of differentiation, and a cell not in the differentiated state and not in the middle of differentiation.

To this end, the discriminator 51 outputs scores representing the cell in the differentiated state and the cell in the middle of differentiation for the input feature quantity and compares the two output scores with corresponding threshold values determined in advance. Then, in a case where the score representing the cell in the differentiated state exceeds the threshold value representing the cell in the differentiated state, and the score representing the cell in the middle of differentiation does not exceed the threshold value representing the cell in the middle of differentiation, a discrimination result that the pixel to be discriminated is the cell in the differentiated state is output. On the other hand, in a case where the score representing the cell in the middle of differentiation exceeds the threshold value representing the cell in the middle of differentiation, and the score representing the cell in the differentiated state does not exceed the threshold value representing the cell in the differentiated state, a discrimination result that the pixel to be discriminated is the cell in the middle of differentiation is output. In a case where both of the two scores do not exceed the corresponding threshold values and in a case where both of the two scores exceed the corresponding threshold values, a discrimination result that the cells are not in the differentiated state and not in the middle of differentiation is output.

Here, as a method of machine learning, a known method can be used. For example, support vector machine (SVM), a deep neural network (DNN), a convolutional neural network (CNN), or the like can be used.

Figure 4:
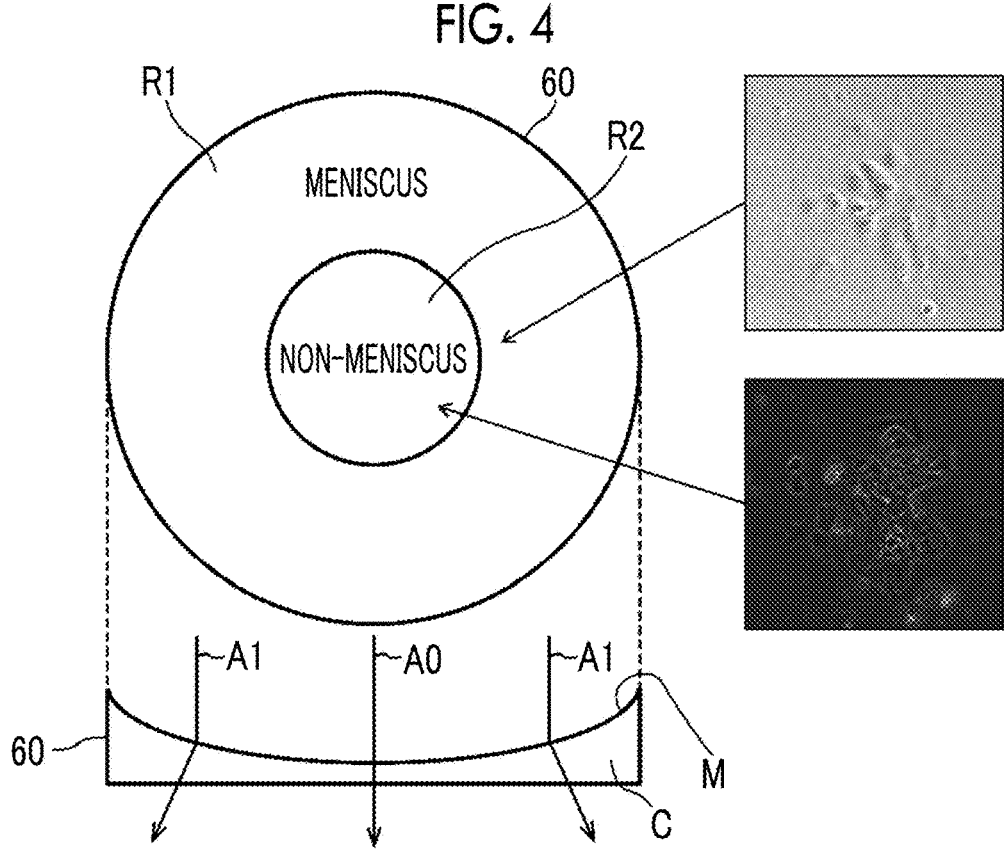
FIG. 4 is a diagram showing a sectional side view and a top view of a cultivation container.
Figure 5:
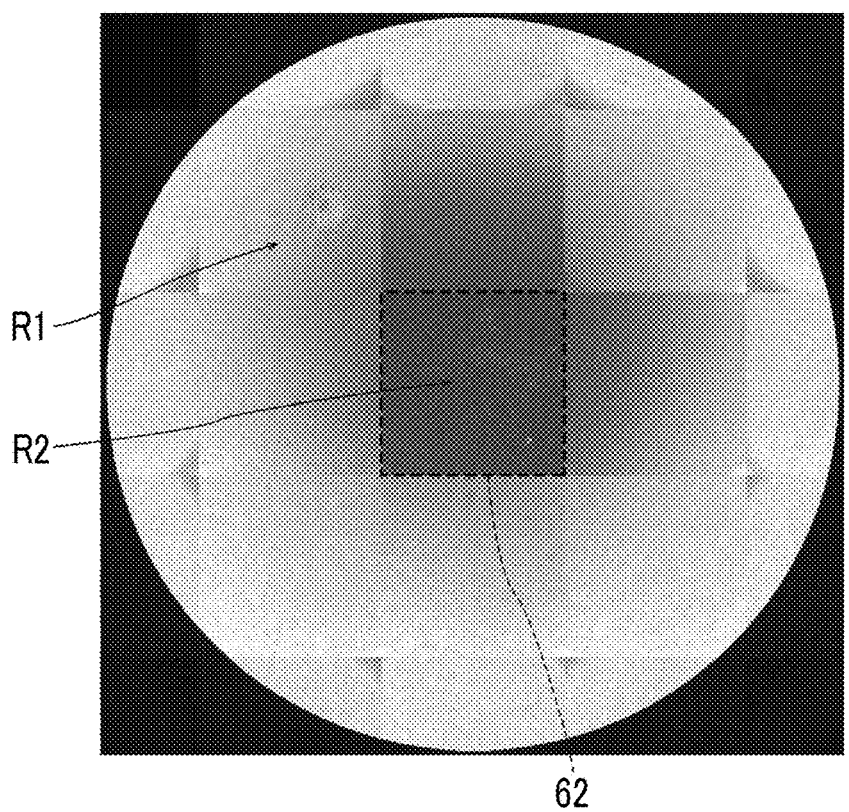
FIG. 5 is a diagram showing an example of an image in which captured images of the observation regions in the cultivation container are linked.

Here, the object S to be observed and the culture solution C are contained in the cultivation container 60, and the meniscus is formed on the liquid surface of the culture solution C. FIG. 4 is a sectional side view and a top view of the cultivation container 60. FIG. 5 is a diagram showing an example of an image in which the captured images of the observation regions in the cultivation container 60 are linked. In FIG. 5, each region 62 divided by a rectangular region corresponds to each observation region. As shown in FIG. 4, a meniscus M is formed on the liquid surface of the culture solution C in the cultivation container 60. Then, light that is incident from above the cultivation container 60 is refracted as indicated by an arrow A1 in a meniscus region R1, and moves forward as indicated by an arrow A0 in a non-meniscus region R2. As a result, as shown in FIGS. 4 and 5, a captured image of the non-meniscus region R2 is high in contrast, and a captured image of the meniscus region R1 becomes lower in contrast than the non-meniscus region R2. Accordingly, for the captured image of the meniscus region R1, an image of an individual cell is not clearly represented. As a result, in the captured image of the meniscus region R1, the accuracy of discrimination of the pixel to be discriminated is degraded.

In the embodiment, in a case where the learning device 52 learns the discriminator 51, a first image including the influence of the meniscus and a second image with the influence of the meniscus eliminated for the same object S to be observed are used.

For this reason, the image acquisition unit 50 acquires the first image including the influence of the meniscus and the second image with the influence of the meniscus eliminated. The first image and the second image are images for the same object S to be observed. Here, the first image may be acquired by imaging the cultivation container 60 as it is.

Figure 6:
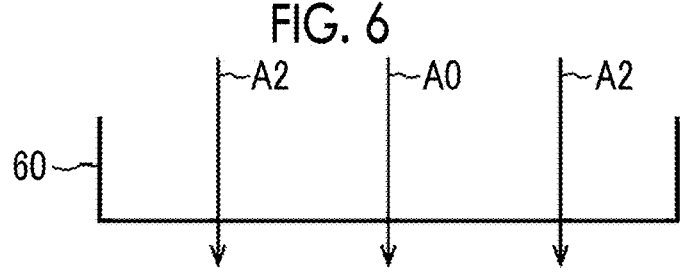
FIG. 6 is a sectional side view showing a state in which a culture solution is eliminated from the cultivation container.

On the other hand, the meniscus M is formed on the liquid surface of the culture solution C in the cultivation container 60. FIG. 6 is a side view of the cultivation container 60 in which the culture solution C is eliminated. As shown in FIG. 6, in a case where the culture solution C is eliminated from the cultivation container 60, light that is incident from above the cultivation container 60 moves forward at any position of the cultivation container 60 as indicated by arrows A0 and A2. Accordingly, the second image is acquired by imaging the object S to be observed in the cultivation container 60 in which the culture solution C is eliminated. In the second image acquired in this way, since the influence of the meniscus M is eliminated, the second image has high contrast regardless of the position on the cultivation container 60.

Figure 7:
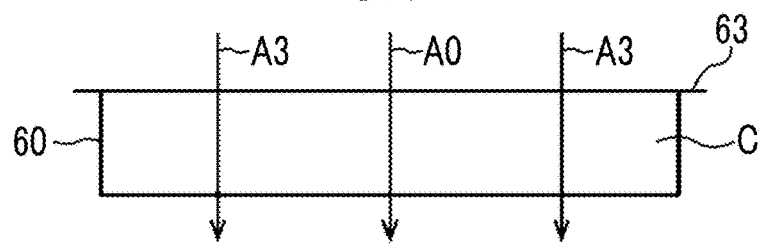
FIG. 7 is a sectional side view showing a state in which the cultivation container is filled with the culture solution and is sealed with a transparent plate.

As shown in FIG. 7, in a case where the cultivation container 60 is filled with the culture solution C, and the cultivation container 60 is sealed with a transparent plate 63, such as transparent glass or plastic, light that is incident from above the cultivation container 60 moves forward at any position of the cultivation container 60 as indicated by arrows A0 and A3. Accordingly, the second image may be acquired by imaging the object S to be observed in the cultivation container 60 that is filled with the culture solution C and is sealed with the transparent plate 63.

Figure 8:
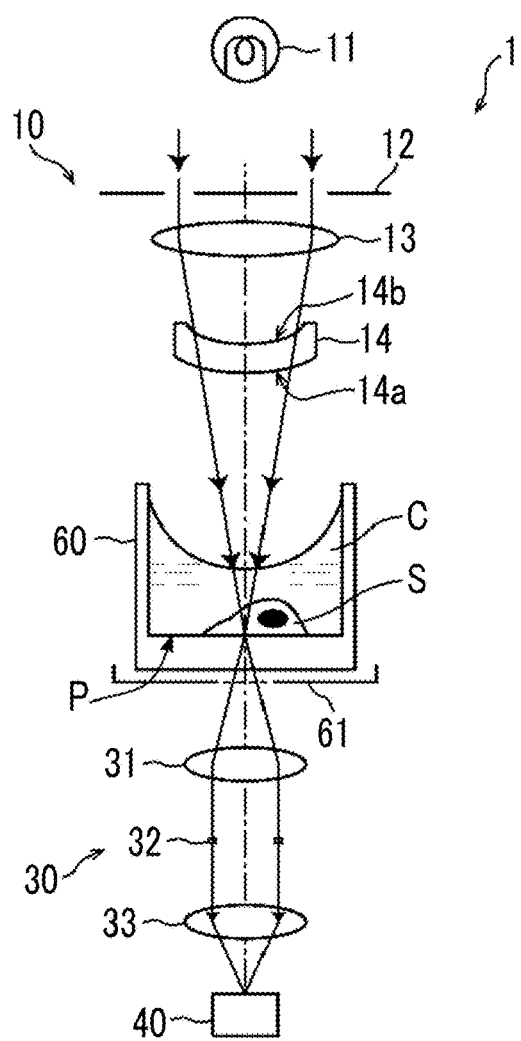
FIG. 8 is a diagram showing the schematic configuration of a microscope device in which an optical element configured to eliminate an influence of a meniscus is provided in an illumination light irradiation unit.

The illumination light irradiation unit 10 may be provided with an optical element that eliminates the influence of the meniscus. FIG. 8 is a schematic view showing the configuration of the microscope device 1 having an illumination light irradiation unit using an optical element configured to eliminate the influence of the meniscus. As shown in FIG. 8, the illumination light irradiation unit 10 is provided with an optical path correction lens 14 as the optical element that eliminates the influence of the meniscus. The optical path correction lens 14 is disposed to be retreatable on an optical path of illumination light in the illumination light irradiation unit 10.

Figure 9:
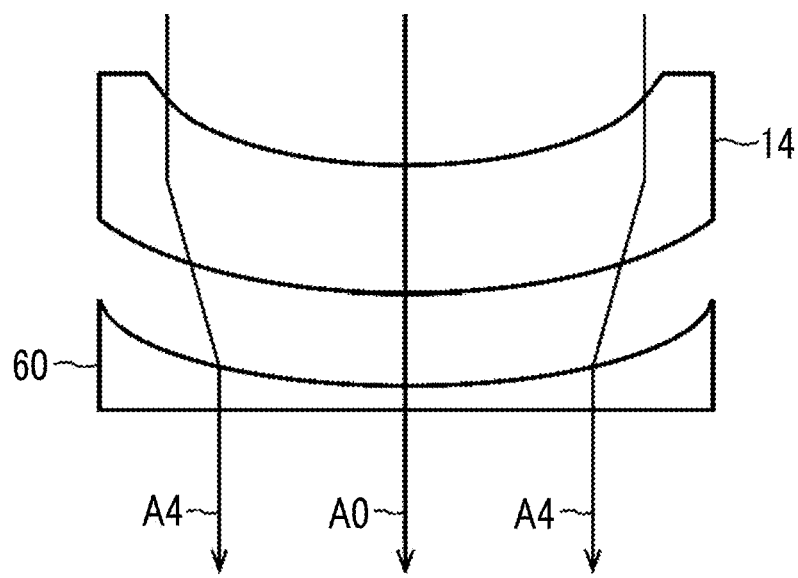
FIG. 9 is a diagram illustrating correction of an optical path using an optical path correction lens.

Specifically, the optical path correction lens 14 has a convex surface 14a on the object S to be observed side, and is a positive meniscus lens, the refractive power of which increases as the distance from the optical axis is greater. At least one of the convex surface 14a on the object S to be observed side or a concave surface 14b on the white light source 11 side of the optical path correction lens 14 may be formed of an aspheric surface. In this way, as the optical path correction lens 14 is provided, as shown in FIG. 9, light that passes through the optical path correction lens 14 and is incident from above the cultivation container 60 moves forward at any position in the cultivation container 60 as indicated by arrows A0 and A4. Accordingly, the second image may be acquired by providing the optical path correction lens 14 in the illumination light irradiation unit 10 and imaging the cultivation container 60.

Figure 10:
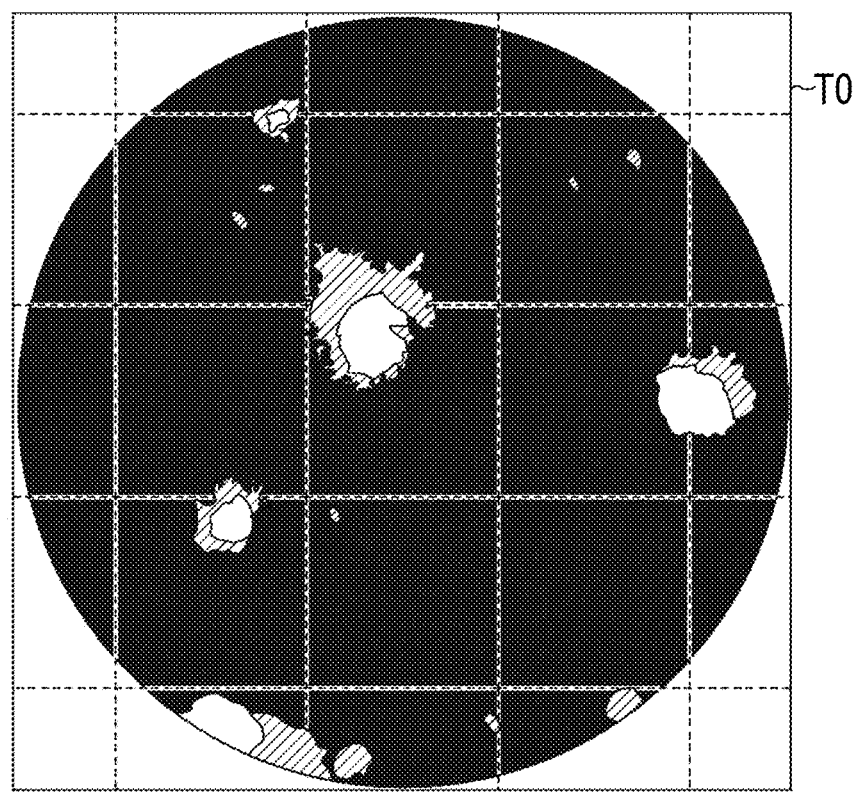
FIG. 10 is a diagram showing an example of training data.

The training data generation unit 53 generates training data for learning the discriminator 51 based on the second image. To this end, the training data generation unit 53 displays the second image on the display device 4. Then, training data is generated by applying a label according to the state of the object S to be observed at each pixel position of the second image through an input from an operator with the input device 3. FIG. 10 is a diagram showing an example of training data. FIG. 10 shows the entire cultivation container 60, and borders of the observation regions are indicated by broken lines. As shown in FIG. 10, in training data T0, a region where the object S to be observed is in a differentiated state is labeled in white, a region where the object S to be observed is in the middle of differentiation is labeled in oblique lines, and a region where there is no object S to be observed is labeled in black. In this way, in training data T0, it is possible to recognize whether the object S to be observed is in a differentiated state or in the middle of differentiation in each pixel.

The learning unit 54 learns the discriminator 51 based on the first image and training data T0. Here, the first image includes the influence of the meniscus M, and the state of the cell as the object S to be observed is not clearly represented in the meniscus region. However, in a case where training data T0 and the first image are associated with each other, it is possible to discriminate the state of the object S to be observed at the individual pixel position of the first image.

To this end, the learning unit 54 inputs the feature quantity of the pixel to be discriminated in the first image to the discriminator 51 and collates the discrimination result output from the discriminator 51 with a pixel in training data T0 corresponding to the pixel to be discriminated. In a case where the discrimination result is a correct answer, the learning unit 54 performs learning of the discriminator 51 to the effect that the discrimination result is a correct answer. In a case where the discrimination result is an incorrect answer, the learning unit 54 performs learning of the discriminator 51 so as to correct the discrimination result. In addition, the learning unit 54 acquires first images and second images for a plurality of objects S to be observed, and generates training data T0 to repeatedly perform learning of the discriminator 51. Then, the learning unit 54 determines whether or not the discrimination result of the discriminator 51 exceeds a correct answer rate determined in advance, and in a case where the determination is affirmative, ends learning of the discriminator 51. The first images and the second images for a plurality of objects to be observed may be acquired in advance and stored in the hard disk (not shown) of the microscope control device 2. In this case, the image acquisition unit 50 acquires the first images and the second images from the hard disk.

The discriminator 51 learned in this way outputs the discrimination result of the state of the pixel to be discriminated in a case where the feature quantity of the pixel to be discriminated in the captured image is input.

Returning to FIG. 1, the input device 3 comprises an input device, such as a keyboard or a mouse, and receives a setting input from the user.

The display device 4 is constituted of a display device, such as a liquid crystal display, and displays the captured image captured in the imaging unit 40, an evaluation result of the captured image, and the like. The display device 4 may be constituted of a touch panel, and thus, may also be used as the input device 3.

Figure 11:
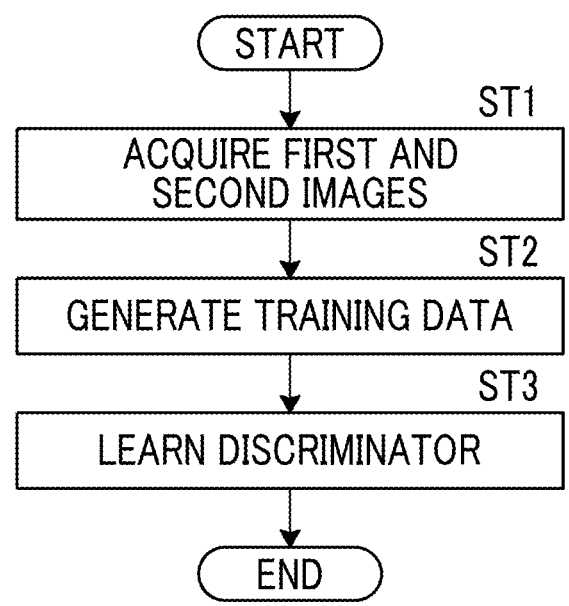
FIG. 11 is a flowchart showing processing that is executed in the embodiment.

Next, processing that is executed in the embodiment will be described. FIG. 11 is a flowchart showing learning processing of the discriminator 51 that is executed in the embodiment. First, the image acquisition unit 50 acquires the first image including the influence of the meniscus M and the second image with the influence of the meniscus M eliminated for the same object S to be observed (Step ST1). Next, the training data generation unit 53 generates training data T0 for learning the discriminator 51 based on the second image (Step ST2). Then, the learning unit 54 learns the discriminator 51 based on the first image and the training data T0 (Step ST3), and ends the processing.

In this way, in the embodiment, the first image including the influence of the meniscus and the second image with the influence of the meniscus eliminated for the same object to be observed are acquired, training data T0 is generated based on the second image, and the discriminator 51 is learned based on the first image and training data T0. For this reason, it is possible to determine whether or not the output of the discriminator 51 is a correct answer with excellent accuracy in a case where the feature quantity of the individual pixel of the first image including the influence of the meniscus is input, and to perform learning of the discriminator 51 with excellent accuracy. As the discriminator 51 learned in this way is used, even in the captured image including the influence of the meniscus, it is possible to discriminate the state of the object S to be observed included in the captured image with excellent accuracy.

In the above-described embodiment, although the captured image formed by the imaging optical system 30 is captured by the imaging unit 40, the imaging unit 40 may not be provided, and an observation optical system or the like may be provided such that the user can directly observe the captured image of the object S to be observed formed by the imaging optical system 30.

In the above-described embodiment, although the invention is applied to the phase contrast microscope, the invention is not limited to the phase contrast microscope, and can be applied to other microscopes, such as a differential interference microscope and a bright-field microscope.

In the above-described embodiment, although the image obtained by applying the label according to the state of the object S to be observed to the second image is used as training data, the second image itself may be used as training data.

According to the above-described embodiment, since the influence of the meniscus M is eliminated in the second image, the state of the object S to be observed in the container is clearly represented in the second image. Furthermore, since training data T0 is generated based on the second image, the state of the object S to be observed is clearly represented even in training data T0. On the other hand, since the first image includes the influence of the meniscus M, the state of the object S to be observed is not clearly represented; however, in a case where the first image and training data T0 are associated with each other, it is possible to clearly discriminate the state of the object S to be observed at the individual pixel position of the first image. Accordingly, as the discriminator 51 is learned based on the first image and training data T0, it is possible to determine whether or not the discrimination result of the discriminator 51 is a correct answer with excellent accuracy in a case where the feature quantity of the pixel position to be discriminated of the first image is used as input. Therefore, it is possible to perform learning of the discriminator 51 with excellent accuracy. Furthermore, as the discriminator 51 learned in this way is used, it is possible to discriminate the state of the object S to be observed included in the captured image with excellent accuracy.

EXPLANATION OF REFERENCES

1: microscope device
2: microscope control device
3: input device
4: display device
10: illumination light irradiation unit
11: white light source
12: slit plate
13: condenser lens
14: optical path correction lens
14a: convex surface
14b: concave surface
21: controller
22: image evaluation device
30: imaging optical system
31: objective lens
32: phase plate
33: imaging lens
40: imaging unit
50: image acquisition unit
51: discriminator
52: learning device
53: training data generation unit
54: learning unit
60: cultivation container
61: stage
62: region
63: transparent plate
70: well plate
71: well
75: scanning start point
76: scanning end point
77: solid line indicating scanning locus
A0, A1, A2, A3, A4: arrow
C: culture solution
M: meniscus
P: installation surface
R1: meniscus region
R2: non-meniscus region
S: object to be observed
T0: training data

What is claimed is:

1. A learning device for a discriminator, which discriminates a state of an object to be observed based on a captured image including an influence of a meniscus acquired by imaging a container, in which a liquid with a meniscus formed on a surface and the object to be observed are contained, the learning device configured to:

acquire a first image including the influence of the meniscus and a second image with the influence of the meniscus eliminated for the same object to be observed;

generate training data for learning the discriminator based on the second image; and learn the discriminator based on the first image and the training data, wherein in the training data, a first region where the object to be observed is in a differentiated state is labeled by a first label, a second region where the object to be observed is in the middle of differentiation is labeled by a second label, and a third region where there is no object to be observed is labeled by a third label, and the first label, the second label, and the third label are each different from each other.

2. The learning device according to claim 1, wherein the second image is acquired by imaging the object to be observed with the liquid eliminated.

3. The learning device according to claim 1, wherein the second image is acquired by imaging the object to be observed in the container filled with the liquid and sealed with a transparent plate.

4. The learning device according to claim 1, wherein the second image is acquired by imaging the object to be observed with an imaging device comprising an optical element configured to eliminate the influence of the meniscus.

5. The learning device according to claim 1, wherein the learning device is further configured to generate an image obtained by applying a label according to the state of the object to be observed to the second image or the second image as the training data.

6. The learning device according to claim 1, wherein the discriminator has a feature quantity of a pixel to be discriminated in the captured image as input, and outputs a discrimination result of the state of the object to be observed for the pixel to be discriminated.

7. The learning device according to claim 1, wherein the captured image is acquired by imaging the container with a phase contrast microscope.

8. The learning device according to claim 1, wherein the learning device is further configured to collate a discrimination result output from the discriminator for a pixel to be discriminated in the first image with a pixel in the training data corresponding to the pixel to be discriminated to learn the discriminator.

9. A discriminator learned by the learning device for a discriminator according to claim 1.

10. A learning method for a discriminator, which discriminates a state of an object to be observed based on a captured image including an influence of a meniscus acquired by imaging a container, in which a liquid with a meniscus formed on a surface and the object to be observed are contained, the learning method comprising:
  acquiring a first image including the influence of the meniscus and a second image with the influence of the meniscus eliminated for the same object to be observed;
  generating training data for learning the discriminator based on the second image; and
  learning the discriminator based on the first image and the training data, wherein
  in the training data, a first region where the object to be observed is in a differentiated state is labeled by a first label, a second region where the object to be observed is in the middle of differentiation is labeled by a second label, and a third region where there is no object to be observed is labeled by a third label, and
  the first label, the second label, and the third label are each different from each other.

11. A non-transitory computer readable recording medium storing a learning program for a discriminator that causes a computer to execute:
  a step of discriminating a state of an object to be observed based on a captured image including an influence of a meniscus acquired by imaging a container, in which a liquid with a meniscus formed on a surface and the object to be observed are contained;
  a step of acquiring a first image including the influence of the meniscus and a second image with the influence of the meniscus eliminated for the same object to be observed;
  a step of generating training data for learning the discriminator based on the second image; and
  a step of learning the discriminator based on the first image and the training data, wherein
  in the training data, a first region where the object to be observed is in a differentiated state is labeled by a first label, a second region where the object to be observed is in the middle of differentiation is labeled by a second label, and a third region where there is no object to be observed is labeled by a third label, and
  the first label, the second label, and the third label are each different from each other.

* * * * *